United States Patent [19]

Buchanan

[11] Patent Number: 5,785,425
[45] Date of Patent: Jul. 28, 1998

[54] FLUID BOILING-POINT SENSING DEVICE

[76] Inventor: Nigel Alexander Buchanan, Beechtree Cottage, New Gilston, by Leven, Fife, KY8 5IF, United Kingdom

[21] Appl. No.: 704,532
[22] PCT Filed: Mar. 13, 1995
[86] PCT No.: PCT/GB95/00543
  § 371 Date: Dec. 9, 1996
  § 102(e) Date: Dec. 9, 1996
[87] PCT Pub. No.: WO95/24646
  PCT Pub. Date: Sep. 14, 1995

[30] Foreign Application Priority Data

Mar. 11, 1994 [GB] United Kingdom ............... 9404701

[51] Int. Cl.$^6$ ........................................ G01N 25/08
[52] U.S. Cl. ........................................ 374/16; 374/25
[58] Field of Search .................. 374/16, 27, 45, 374/50, 57, 147, 148, 164, 170, 208; 73/61.43, 61.76

[56] References Cited

U.S. PATENT DOCUMENTS

| | | | |
|---|---|---|---|
| 1,443,537 | 1/1923 | Hortvet | 374/16 |
| 3,276,262 | 10/1966 | Sapoff et al. | 374/27 |
| 3,940,988 | 3/1976 | Reed | 374/148 |
| 4,781,469 | 11/1988 | Turon-Lagot | 374/27 |
| 4,958,937 | 9/1990 | Lohberg et al. | 374/16 |
| 4,987,749 | 1/1991 | Baier | 374/148 |
| 5,380,091 | 1/1995 | Buchanan | 374/16 |

FOREIGN PATENT DOCUMENTS 2338489 8/1977 France.
WO9012311 10/1990 WIPO.

*Primary Examiner*—G. Bradley Bennett
*Attorney, Agent, or Firm*—Lalos & Keegan

[57] ABSTRACT

A Portable Fluid Boiling Point Sensing Device (1) which can be used to measure the boiling point of fluids. The device includes a probe (2) for immersion in fluid to be tested, in particular in fluid reservoir. The probe (2) comprises a casing (2a) defining a chamber (3) for a semi-encapsulated portion of fluid (3a). The fluid (3a) kept at an optimum level without sensitive probe (2) depth measurement by a quantity of air (4) being trapped above an aperture means (6a) on the casing (2a) causing an artificial fluid level ($L_1$) to be maintained below the surface of the test fluid. A heater (8) and a temperature sensor (9) are present in the housing (2a) and apertures (5, 6a, 6b) are provided to permit fluid flows into and from the chamber (3). The device senses the boiling temperature of the fluid by measuring the temperature of the vapors (11) given off the heated fluid (3a) within the housing (3), or alternatively directly from the fluid (FIG. 5a/b).

20 Claims, 5 Drawing Sheets

FLUID BOILING-POINT SENSING DEVICE

The present invention relates to a device for sensing the boiling point of a fluid and, more especially relates to a device for conveniently sensing the boiling point of hydraulic fluid, for example for testing the quality of brake fluid of a motor vehicle.

A hydraulic fluid such as motor vehicle brake fluid is hygroscopic, i.e. absorbs water (moisture). Water absorption has, of course, the effect of considerably reducing the boiling point of the fluid, with the result that in the case of motor vehicles, heavy vehicle braking may give rise to sufficient heat generation to boil the brake fluid thereby resulting in vapour entrapment in the fluid which could dangerously reduce braking performance.

Consequently, there is the need to test the quality brake fluid by sensing the boiling point of the fluid, so that the sensed value can be compared with an accepted standard to evaluate the fluid quality. Sensing devices are known for sensing the boiling point of fluid and especially the boiling point (and quality) of brake fluid. Basically, these devices include a heater to heat a quantity of the fluid to boiling point and a temperature sensor to sense the boiling temperature. Some of these devices, e.g. as shown in U.S. Pat. No. 4,958,937, require a sample of fluid to be removed from the vehicle reservoir for testing, and the subsequent testing procedure is of a somewhat delicate laboratory-like nature. This is inconvenient and is not readily acceptable for everyday garage operations. To meet this problem, other sensing devices have been provided capable of testing directly at the fluid reservoir, an example of such a device being shown in U.S. Pat. No. 4,484,823 (WO90 12311), but the arrangement of the heating means in the device of U.S. Pat. No. 4,484,823 precludes prompt temperature sensing. The device shown in International Application WO90/12311 overcomes this problem by providing a hand-held sensor which, when inserted into the fluid to be tested, traps a small portion of the fluid in a semi-encapsulated chamber in a probe part of the device for heating. The device, however, relied very much on correct depth immersion in the fluid. It is an object of the present invention to provide a fluid boiling-point sensing device which is capable of being hand-held and which can be used in a more convenient manner to sense the boiling points of fluids directly at a fluid reservoir, e.g. in a vehicle brake fluid reservoir.

Therefore, the present invention is provides a fluid boiling-point measuring device as set out in the appended claim 1.

Therefore, the first aperture means on the outer surface of the probe constitute to control means controlling the level of the fluid in the housing for different degrees of immersion of the probe and further said control means serves to keep the test fluid in the housing at a set level by trapping a quantity of air within the probe above the aperture means such as to maintain a fluid/air boundary at a set level.

Preferably further aperture means are located below the bottom of the temperature sensor.

Preferably the probe member is of cylindrical form, said upper and lower housing portions defining cylindrical chambers, a plug being providd to close the top of the chamber of the upper housing portion. The probe member may comprise a single cylindrical casing, with said first aperture means located on a bottom wall of the casing. Alternatively the probe member may be of radially spaced double-wall form with said second aperture means on the outer wall and additional fluid aperture means on the inner wall located above said second aperture means. Either of the first and second aperture means may comprise openings of a restricted form. The heating means preferably comprise an electrical heater supplied with power from an electrical battery while the temperature sensor which can comprise a thermocouple device is preferably linked to suitable monitoring and presentation means for registering the measured temperature value. The probe member is preferably part of a self-contained hand-held unit.

In a preferred embodiment the fluid heating means are located around a central conduit, said central conduit having aperture means top and bottom and located within said conduit is a temperature sensor preferably of an electronic type. Said probe member further includes a second part located above said first housing part and open at the bottom so as to be in fluid communication with said first part via centre apertures, allowing fluid communication with the fluid within said conduit.

Said upper housing portion can have the first aperture means within the probe outer side wall (preferably cylindrical) serving for discharging fluid air from the probe member to a fluid reservoir surrounding the probe and arranged so that when the said probe member is inserted into the reservoir fluid air is trapped in the closed topped upper housing portion to maintain a fluid boundary between said housing portion. When the said probe is inserted into the fluid to be tested to a depth past said first aperture means and the heating means operated, the fluid within the lower housing portion is heated. The gap between the said outer side wall and the central conduit can allow the heated test fluid to rise, pulling cooler fluid from the base of probe. By restricting the size of the the aperture means at the probe base, the heated fluid is drawn down the conduit means causing a convection flow of the fluid being tested rising to the top of the lower housing portions of the probe and being drawn down the central conduit past the temperature sensor agitating the test fluid within the said lower housing portion part. The fluid boundary between the upper and lower housing portions restricts heat fluid heat transfer to the second part so causing the temperature to stabilise within the lower housing portion at boiling point. If the temperature within the lower housing portion were to rise to such a level that the boiling of the test fluid causes excessive gas bubbles within the lower housing portion, these excessive gas bubbles will be vented via the fluid boundary and through the first aperture means. Cooler fluid from the reservoir is received into the first part via the first aperture means compensating for the evaporated test fluid within the lower housing portion and tending to stabilise the test fluid temperature at its relevant boiling point.

By the above arrangement, accurate testing of fluid in a reservoir is possible irrespective of the depth of immersion of the probe member in the fluid, provided that the first aperture means are below the level of the fluid in the reservoir.

Embodiments of the present invention will now be described by way of example with reference to the accompanying drawings wherein.

Figure 1:
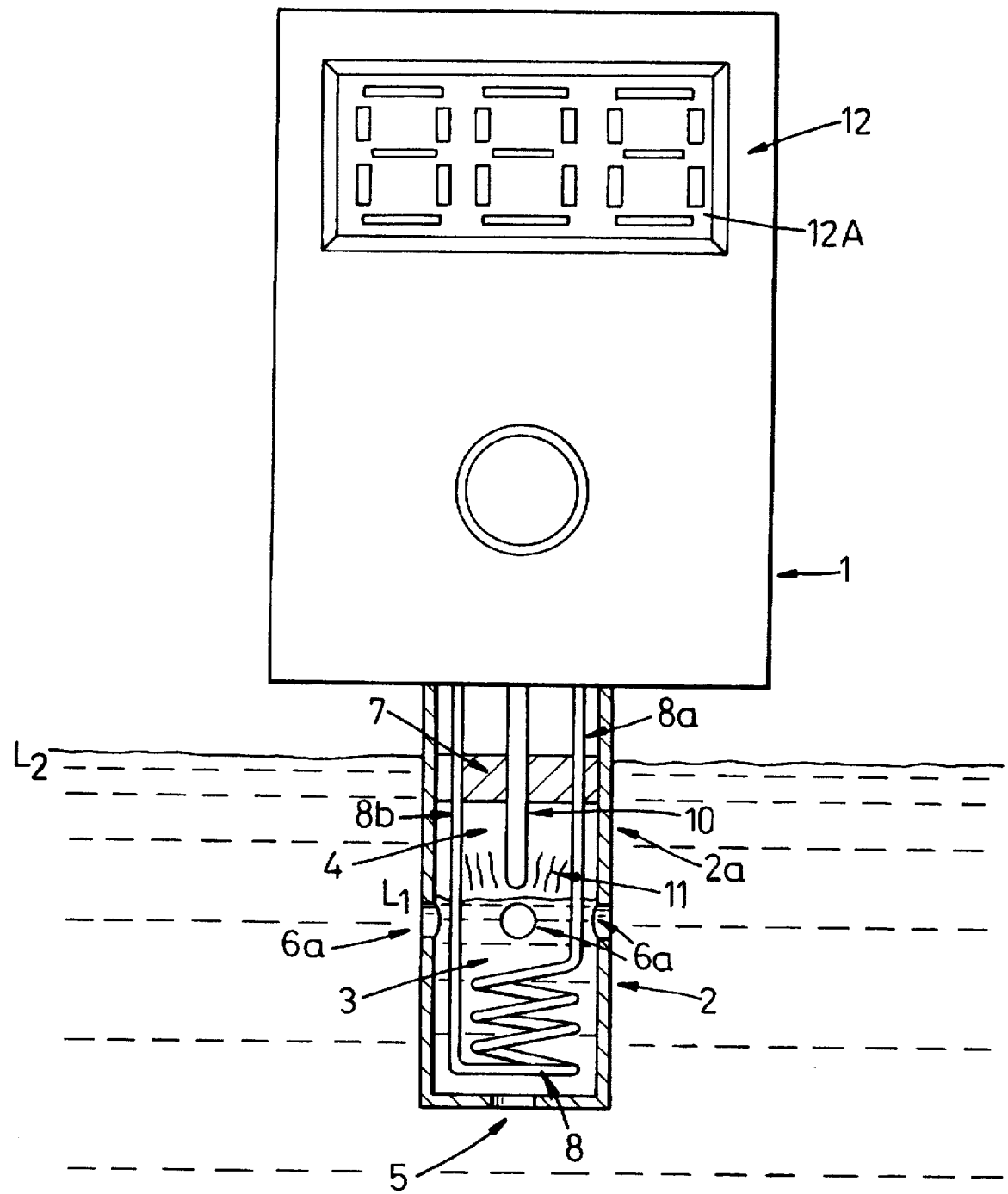
FIG. 1 shows a sectional elevation of a probe member of a brake fluid tester or analyser, in accordance with one embodiment of the present invention.

Referring to FIG. 1, a portable hand-held analyser or tester (generally indicated by ref 1) serves to sense the boiling temperature of a fluid, especially automotive brake fluid, so that the quality of the fluid can be established, the tester 1 including probe member 2 for insertion into fluid to be tested. The probe member 2 comprises a lower part 3 and an upper part 4 thereabove, aperture means 5 at the bottom of the prove permitting fluid flow into the part 3, and aperture means 6a for discharge of fluid from the probe membr 2. The top of the aperture means 6a where at a fluid level $L_1$, is established in the member 2 generally defines the demarcation line between the lower and upper parts 3, 4 the upper part 4 being in fluid communication with the lower part 3. The member 2 is of cylindrical form so that the parts 3, 4 comprise cylindrical chambers or housings.

The upper part 4 is closed at its top end by a plug 7. The lower part 3 houses an electrical heating element 8 the leads 8a, 8b of which pass sealingly through the plug 7 while a temperature sensor 10 is located in the part 4 so that the sensor bottom end is just above the $L_1$, and serves for measuring the boiling point of fluid heated in the part 3, the sensor 9 also passing sealingly through the plug 7.

Figure 2A:
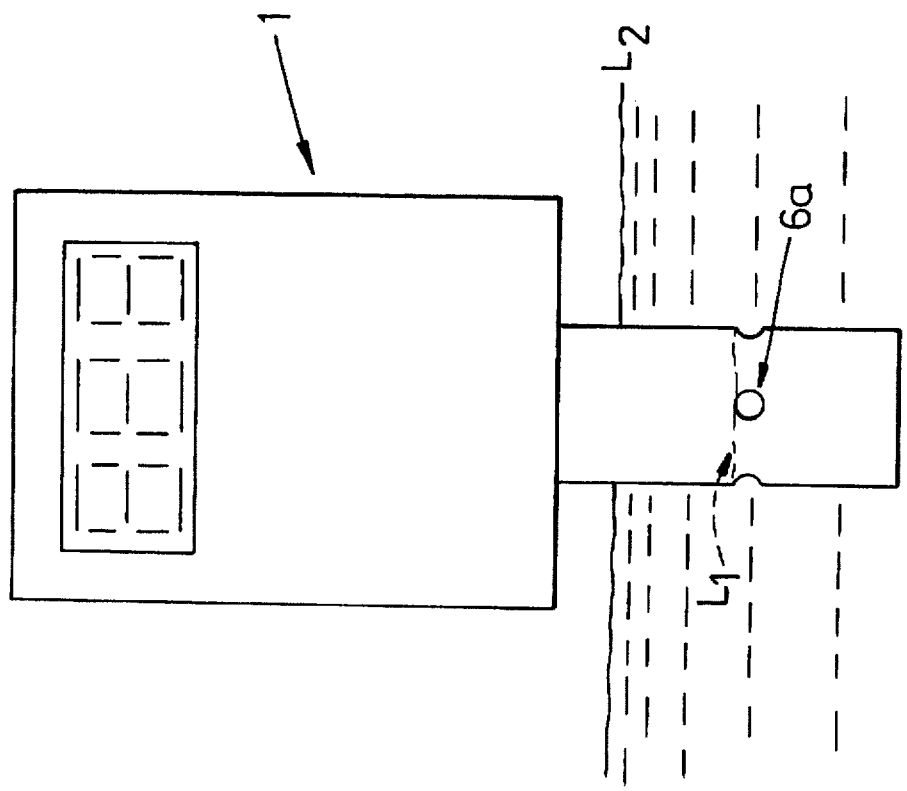
FIGS. 2a and 2b show pictorial views illustrating the use of the tester of FIG. 1.
Figure 3:
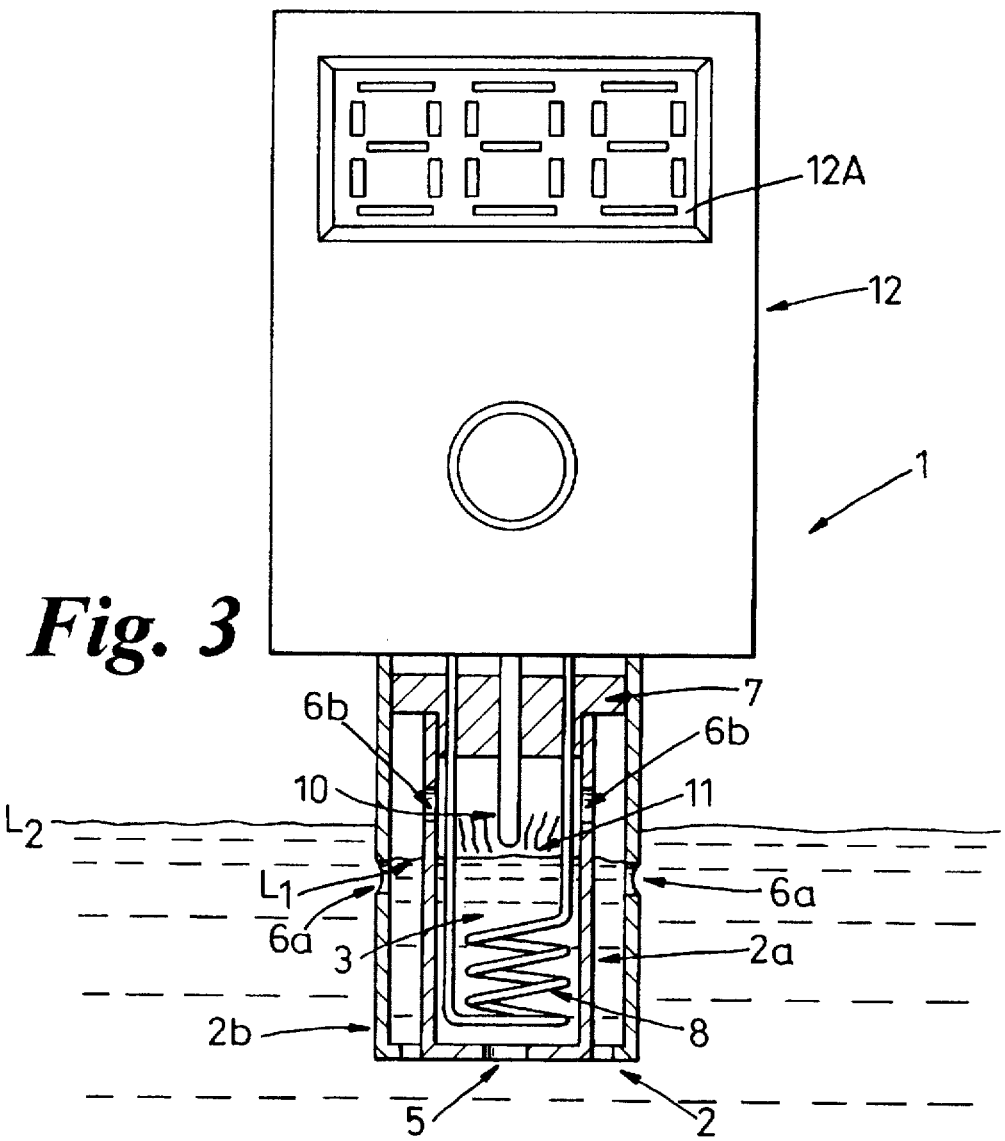
FIG. 3 shows a view similar to FIG. 1 of a second embodiment of the present invention.

FIG. 3 shows a similar arrangement but with double cylindrical walls 2a, 2b providing insulation for the housing part 3. The inner wall 2a includes aperture means 6b at the upper end whereby gas vapour 11 emitted from fluid under test in the housing 3 and passing from surface $L_1$, can flow to the aperture means 6a via the annular passage between the walls 2a, 2b. The aperture means 6a preferably comprise a plurality of individual ports 6a (in particular at least four) arranged around the circumference of the wall 2b at approximately the same level: this enables the device 1 to operate even whe tilted (as shown dashed in FIG. 2a) up to 45° from the vertical.

Figure 4:
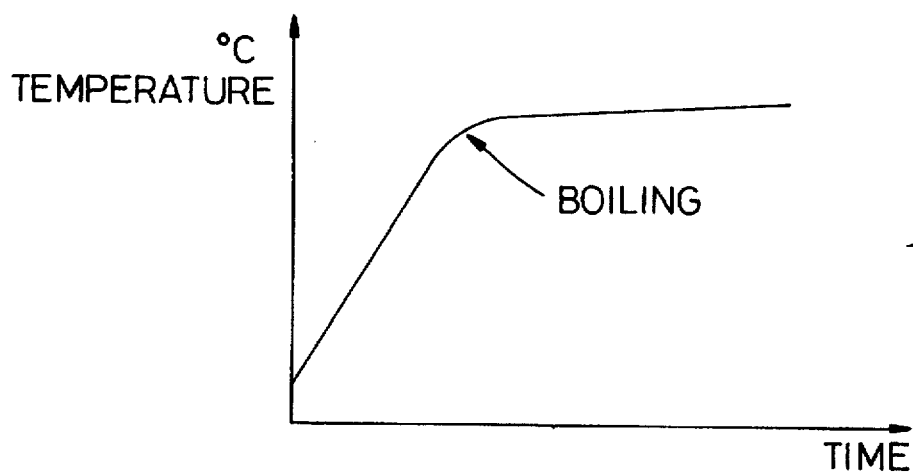
FIG. 4 shows a graph of the temperature of fluid under test and heated in the tester against time.

The temperature sensor 10 can comprise a thermocouple device which is linked to electronic measurement processing equipment housed in a display unit 12. Such electronic processing equipment is well established and consequently need not be described in detail; the equipment (and the heater 8) can be powered by self-contained rechargeable batteries or alternatively leads can be included to couple the equipment to a separate battery e.g. the motor vehicle battery. The temperature measurement is shown on a display 12a of the unit 12. Additionally the equipment includes a latching device responsive to the rising temperature measurement of the sensor (thermocouple) 10 (in this case the temperature of the vapour 11), and the latching device is such that as the temperature rise reduces and stabilises as the boiling temperature is approached and reached (as shown in FIG. 4) the device latches to the stabilised temperature and this is indicated on display 12A. The stabilized temperature being latched on by the device and the corresponding temperature is shown on the display until the device is switched off or the next test sequence begun.

Figure 2B:
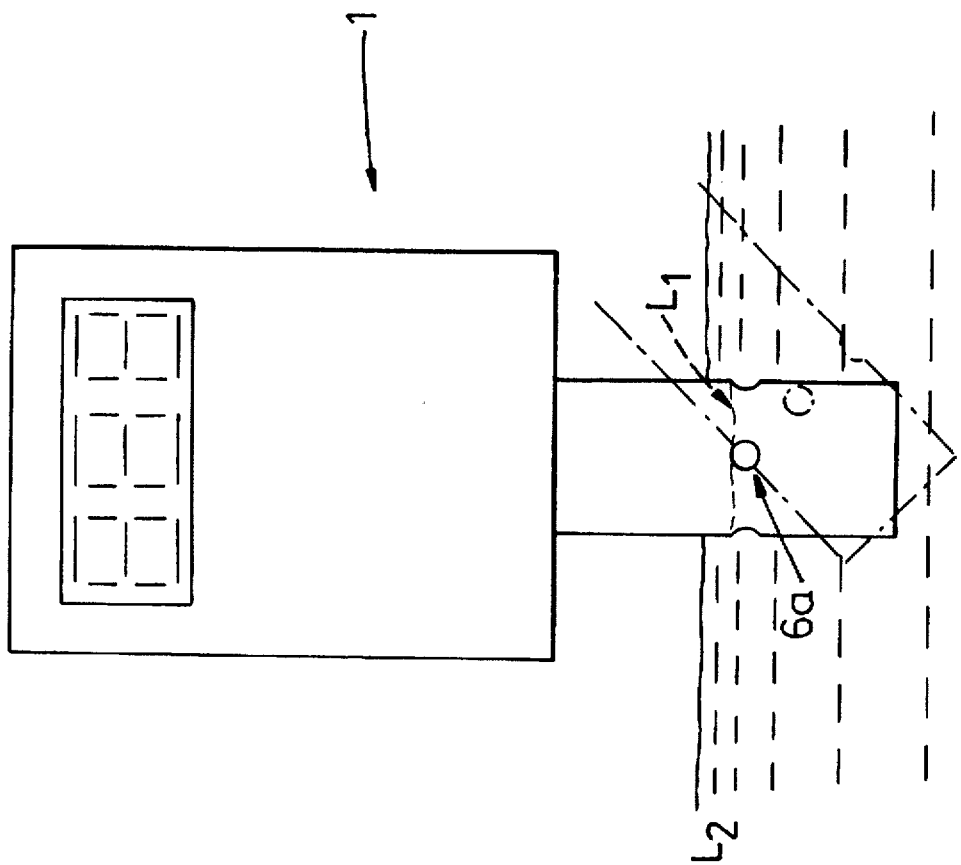

A significant feature of the device 1 is the provision of a closed air space 4 between the upper plug 7 and the level at the apertures 6a, this space 4 effectively providing an air buffer which enables the device 1 to enjoy several significant characteristics, namely:

a) The device is not excessively immersion depth sensitive as the level $L_1$, of the test fluid in the probe 2 can be maintained substantially uniform for varying degrees of probe immersion as shown in FIGS. 2a and 2b.

b) Fluid disturbance in the probe 2 of the device 1 is minimised due to the air buffer absorbing fluid pressure fluctuations in the probe thereby preventing escape of hot fluid from the probe.

c) The air buffer provides thermal insulation between the hot fluid in the housing 3 and the processing equipment in unit 12.

The aperture 5 or apertures in the base of the probe 2 preferably have a size which allows the fluid to flow timeously into the test housing 3 while restricting the flow of oxygen in the probe 2. The advantage of this is that if the device were inadvertently operated when outwith the fluid reservoir i.e. with the probe in air the possibility of the residue fluid within the probe being set alight is avoided or reduced. A further characteristic of the present invention is that the probe 2 when immersed in the test fluid past the probe apertures 6a in the outer probe casing becomes largely insensitive to the depth of fluid being tested until immersed to such a level that the pressure within the lower housing portion starts to compress the air pocket in the probe above the fluid thereby altering the fluid air boundary $L_1$.

Figure 5A:
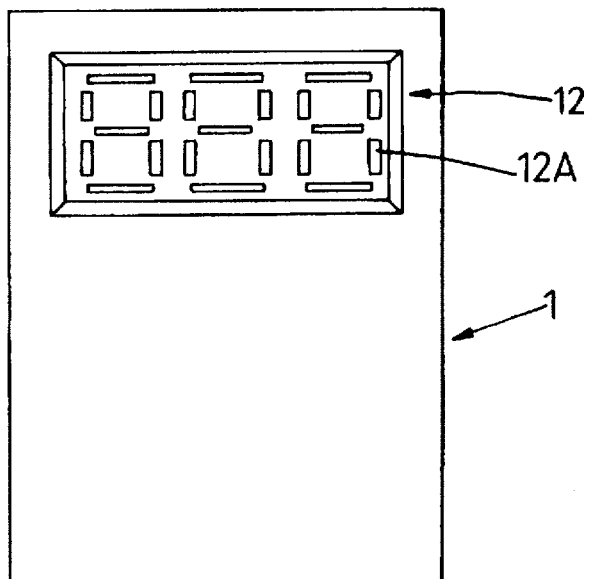
FIGS. 5a and 5b show a sectional elevation of a probe member of a brake fluid tester or analyser, in accordance with a further embodiment of the present invention.
Figure 5B:
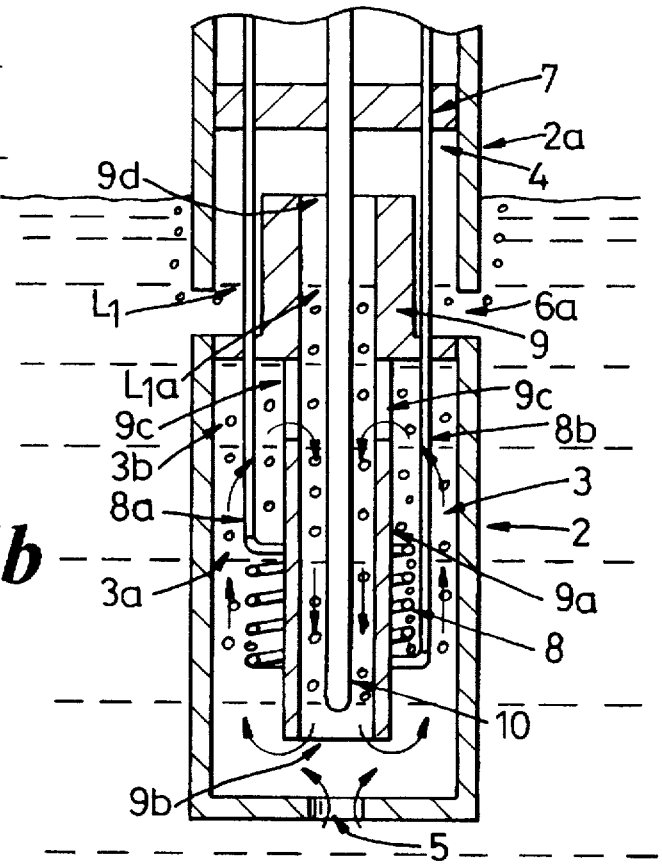

In the embodiment of FIGS. 5a/5b where the boiling point temperature is sensed somewhat differently, a portable hand-held analyser or tester (generally indicated by ref 1), again includes a probe member 2 comprising a lower part 3 and an upper part 4 thereabove, aperture means 5 permitting fluid flow into the part 3, and aperture means 6a for discharge of fluid from the probe member 2 within the upper part 4 level. The top of the aperture means 6a where at a fluid level L. La is established in the member 2 generally defines the demarcation line between the lower and upper parts 3, 4, the upper part 4 being in fluid communication with the lower part via aperture means 9d in a plug 9. The member 2 is of cylindrical form so that the parts 3, 4 comprise cylindrical chambers. The upper chamber 4 is closed at its top end by a plug 7. The lower chamber 3 houses an electrical heating element 8 and its leads (8, 8b) which pass sealingly through the plug 7 and the second plug 9 serving to separate the upper chamber 4 and lower chamber 3. Extending from the base of the second plug 9 is a conduit (tube) 9a with lower aperture 9b. Apertures 9c are level with the top of the lower chamber 3 and the upper chamber 4 and lower chamber 3 are fluidly connected through aperture 9d. A temperature sensor 10 is located within the conduit 9a and serves for measuring the boiling point of fluid heated in the lower chamber 3, as shown in FIG. 5b. The heated fluid 3a rises and causes the same heated fluid to be drawn down the central conduit 9a via apertures 9c, 9b so that fluid recirculation is established. The temperature within this circulating fluid 3a stabilises at the boiling point. Excessive steam bubbles 3b if created within the lower chamber 3 vent through the fluid boundary L, La and aperture 6a, cooler fluid from the reservoir being drawn in through aperture 5 helping to stabilise the fluid's 3a temperature.

Figure 6:
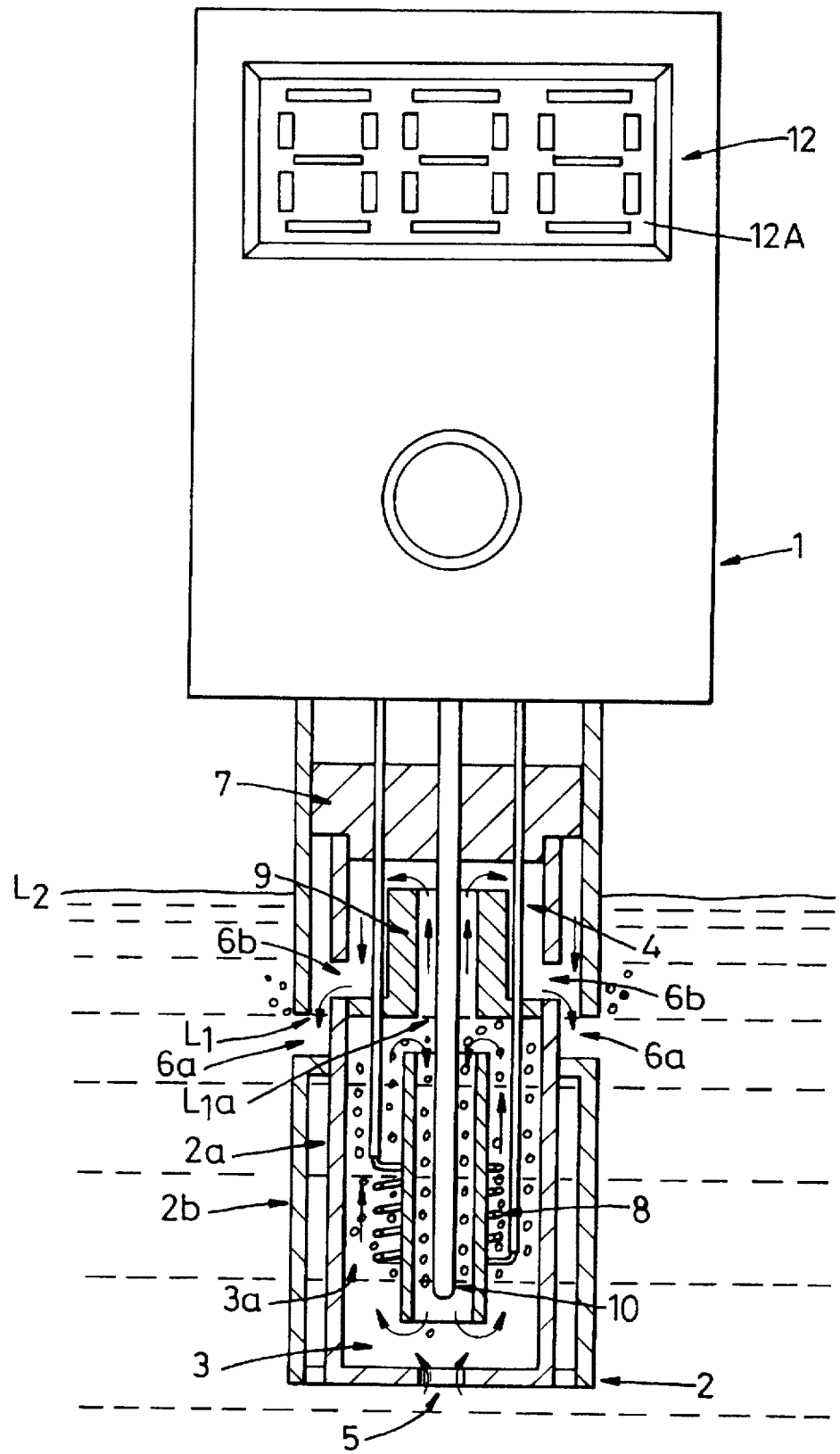
FIG. 6 shows a view similar to FIG. 5a/b of yet a further embodiment of the present invention.

The embodiments of FIGS. 5a/b and FIG. 6 also employ the air buffer 4 of the FIG. 1 embodiment and a temperature measurement processing equipment in a display unit 12 and including a latching device is again provided, temperature measurements and latching in this case being taken directly from the fluid rather than from the emitted vapour as in the earlier embodiments.

Instead of the combined display unit 12 and probe 2, it would be possible to have a remote display unit 12 connected to the probe 2 by cable means.

In FIGS. 1 and 3, the bottom of the temperature sensor may extend slightly below the surface L, of the test fluid in housing 3 but nevertheless for the sensor to be essentially responsive to the temperature of the emitted vapour 11.

I claim:

1. A fluid boiling point sensing device for indicating the boiling point of fluid, especially a hygroscopic fluid such as hydrauling fluid, comprising a meter including a probe for insertion into fluid in a fluid reservoir, heating means being provided in the probe for heating fluid within the probe when the probe is immersed, said meter additionally including monitoring means for monitoring the temperature rise of fluid heated by said heating means so as to indicate the boiling point temperature of the fluid, said probe including a casing defining a housing having a top end and a bottom end, said top end being closed, first aperture means on the casing spaced from the level of the top end of the housing whereby when the probe is inserted in fluid with said first aperture means below the surface of said fluid, an air/fluid boundary is formed in the housing adjacent the level of said first aperture means and demarcating lower and upper housing portions such that in said lower housing portion fluid to be tested is retained and in said upper housing portion above said lower housing portion air is retained, said upper housing portion being in fluid communication with said lower housing portion, said temperature monitoring means sensing the temperature of fluid in said lower housing portion heated by the heating means, and fluid inlet means permitting fluid flows to and from the housing.

2. A fluid boiling point sensing device as claimed in claim 1, wherein the probe is arranged to enable the test fluid to flow into said lower housing portion so as to semi-encapsulate a portion of the fluid to be tested in the housing, said air being retained in the upper housing portion by trapping a quantity of air in said upper housing portion above the first aperture means, a fluid circulation being maintained within the lower housing portion by heating of the fluid by the heating means.

3. A fluid boiling point sensing device as claimed in claim 1, wherein a secondary tube is provided in the lower housing portion of the casing, upper and lower apertures being located in said secondary tube for the promotion of a recirculatory flow of test fluid via the inside of the tube and the annular space between the tube and the casing.

4. A fluid boiling point sensing device as claimed in claim 1, wherein there is provided a display means wherein the temperature of the fluid on test as it reaches boiling point is indicated.

5. A fluid boiling point sensing device as claimed in claim 4, wherein said display means comprises an electronic means.

6. A fluid boiling point sensing device as claimed in claim 4, wherein there is provided a latching device which senses the rise in the temperature of the fluid being tested as it is heated, the arrangement being such that as the temperature rise lessens, then levels as the test fluid boiling point occurs, the latching device latches on to this stabilised temperature and the corresponding temperature is shown in the display means until there occurs any one of the device being switched off and the next test sequence begun.

7. A fluid boiling point sensing device as claimed in claim 1, wherein the casing includes a base wall, and an aperture means is provided in the base wall allowing the fluid to pass into the lower housing portion when the probe is immersed past a set fluid level and also facilitating fluid to flow from within the probe when the probe is withdrawn from the fluid, the aperture means in the base wall being of a size which allows the fluid to flow timeously into the lower housing portion while restricting the flow of oxygen onto the heating means.

8. A fluid boiling point sensing device as claimed in claim 6, wherein the air retained in the upper housing portion forms a thermal buffer between the heated test fluid and the latching and display means.

9. A fluid boiling point sensing device as claimed in claim 1, wherein the probe is arranged to be largely insensitive to the depth of fluid being tested until the probe is immersed to such a level that the pressure of the fluid in the lower housing portions starts to compress the air within the upper housing portion thereby altering the fluid/air boundary.

10. A fluid boiling point sensing device as claimed in claim 3, wherein a plug is provided in the casing above said secondary tube so as to be positioned at the boundary of said upper and lower housing portions, said plug including a through-bore communicating with the inner space of the secondary tube for fluid communication between the upper and lower housing portions, said first aperture means being spaced from the top end of the housing so as to be close to the level of said upper aperture of the secondary tube thereby mitigating against the formation of hot spots at the air/fluid boundary of the housing portions.

11. A fluid boiling point sensing device as claimed in claim 3, wherein said casing is of double wall form comprising an outer primary casing and an additional annular wall between said secondary tube and the primary casing whereby heated fluid in the lower housing portion circulates upwards between the secondary tube and the annular wall and downwards via the inner space of the secondary tube until the temperature of the fluid is uniform within the lower housing portion, the arrangement permitting excess vapour produced on heating of the test fluid to escape via the upper housing portion and said first aperture means, while the cooler fluid entering the lower housing portion via said fluid inlet means serves to stabilise the test fluid at its boiling point temperature, the space between the primary casing and said annular wall constituting an insulation space surrounding the heated fluid in the lower housing portion.

12. A fluid boiling point sensing device as claimed in claim 11, wherein said annular wall extends into the upper housing portion and the upper end of the space between the primary casing and the annular wall is sealingly closed by a closure plug also serving as the closure of the upper end of the upper housing portion, the annular wall including port means in the upper housing portion to permit escape of vapour to said first aperture means.

13. A fluid boiling point sensing device as claimed in claim 1, wherein the temperature monitoring means extends into said lower housing portion.

14. A fluid boiling point sensing device as claimed in claim 3, wherein the heating means includes a heating element surrounding said secondary tube.

15. A fluid boiling point sensing device for indicating the boiling point of fluid, especially a hygroscopic fluid such as hydraulic fluid, comprising a meter including a probe for insertion into fluid in a fluid reservoir, heating means being provided in the probe for heating fluid within a housing in the probe when the probe is immersed, said meter additionally including monitoring means for monitoring the temperature rise of fluid heated by said heating means so as to indicate the boiling point temperature of the fluid, said probe including a casing retaining said fluid to be tested and fluid inlet means permitting fluid flow to and from the housing and including an aperture on the bottom of the casing wherein said probe comprises a single peripheral walled structure defining said housing, said fluid inlet means including first aperture means on the single peripheral wall permitting flow of liquid to or from said housing when the probe is immersed and positioned such a that a liquid level is established in the housing demarcating a lower housing portion for liquid to be tested and an upper housing portion above said lower housing portion defining an air zone which is in fluid communication with the liquid to be tested in said lower housing portion, said temperature monitoring means sensing the temperature of liquid in said lower housing portion heated by the heating means.

16. A fluid boiling point sensing device as claimed in claim 15, wherein the temperature monitoring means is located slightly above the level of the first aperture means.

17. A fluid boiling point sensing device for indicating the boiling point of fluid, especially a hygroscopic fluid such as hydraulic fluid, comprising a meter including a probe for insertion into fluid in a fluid reservoir, heating means being provided in the probe for heating fluid within a housing in the probe when the probe is immersed, said meter additionally including monitoring means for monitoring the temperature rise of fluid heated by said heating means so as to indicate the boiling point temperature of the fluid, said probe including a casing retaining said fluid to be tested and fluid inlet means permitting fluid flows to and from the housing and including an aperture on the bottom of the casing wherein said probe comprises radially spaced annular walls, said inlet means including first aperture means on the outermost annular wall permitting liquid flow to or from said housing when the probe is immersed and positioned such that a liquid level is established in the housing creating a lower housing portion for liquid to be tested in the internal space of the innermost annular wall and an upper housing portion above said lower housing portion defining an air zone which is in fluid communication with the liquid to be tested in said lower housing portion, said heating means being located in said lower housing portion, said innermost annular wall comprising a tube providing second aperture means located above the level of said first aperture means so as to be in said air zone, said temperature monitoring means sensing the temperature of liquid in said lower housing portion heated by the heating means.

18. A fluid boiling point sensing device as claimed in claim 17, wherein said second aperture means are located on the peripheral wall of said tube.

19. A fluid boiling point device as claimed in claim 17, wherein the temperature monitoring means is located slightly above the level of the first aperture means.

20. A fluid boiling point sensing device for indicating the boiling point of fluid, especially a hygroscopic fluid such as hydraulic fluid, comprising a meter including a probe for insertion into fluid in a fluid reservoir, heating means being provided in the probe for heating fluid within a housing in the probe when the probe is immersed, said meter additionally including monitoring means for monitoring the temperature rise of fluid heated by said heated means so as to indicate the boiling point temperature of the fluid, said probe including casing means defining said housing wherein the fluid to be tested is retained and fluid inlet means permitting fluid flows to and from the housing of the probe comprising an outer casing and an inner tube said fluid inlet means including first aperture means on the outer casing permitting liquid flow to or from the housing when the probe is immersed and positioned such that a liquid level is established in the housing creating a lower housing portion for liquid to be tested and an upper housing portion above the lower housing portion defining an air zone which is in fluid communication with the liquid to be tested in the lower housing portion, said heating means being located in the lower housing portion while said inner tube includes upper and lower aperture means below said liquid level whereby a recirculation flow of heated liquid can be established in said lower housing portion which flow passes through said inner tube via said upper and lower aperture means, said temperature monitoring means sensing the temperature of liquid in said lower housing portion heated by said heating means.

* * * * *